(12) United States Patent
Tubbs

(10) Patent No.: US 7,488,107 B2
(45) Date of Patent: Feb. 10, 2009

(54) METHOD AND APPARATUS TO DETECT AND CORRECT ALIGNMENT ERRORS IN X-RAY SYSTEMS USED TO GENERATE 3D VOLUMETRIC IMAGES

(75) Inventor: David Austin Tubbs, Sandy, UT (US)

(73) Assignee: General Electric Company, Schenectady, NY (US)

( * ) Notice: Subject to any disclaimer, the term of this patent is extended or adjusted under 35 U.S.C. 154(b) by 447 days.

(21) Appl. No.: 11/207,678

(22) Filed: Aug. 18, 2005

(65) Prior Publication Data
US 2007/0041508 A1    Feb. 22, 2007

(51) Int. Cl.
*A61B 6/08*    (2006.01)
*G01D 18/00*    (2006.01)

(52) U.S. Cl. ........................... 378/205; 378/207
(58) Field of Classification Search .................. 378/19, 378/20, 98.8, 162–164, 205, 207
See application file for complete search history.

(56) References Cited

U.S. PATENT DOCUMENTS

| | | | |
|---|---|---|---|
| 3,940,617 A | 2/1976 | Farnum et al. |
| 4,033,884 A | 7/1977 | Lorch et al. |
| 4,047,034 A | 9/1977 | Auphan |
| 4,126,789 A | 11/1978 | Vogl et al. |
| 4,134,018 A | 1/1979 | Weinkauf et al. |
| 4,191,892 A | 3/1980 | Huang et al. |
| 4,355,230 A | 10/1982 | Wilson et al. |
| 4,506,375 A | 3/1985 | Manson |
| 4,965,065 A | 10/1990 | Lukacsko et al. |
| 5,029,337 A | 7/1991 | MacKenzie et al. |
| 5,206,174 A | 4/1993 | Gehrke et al. |
| 5,261,977 A | 11/1993 | Powell |
| 5,333,168 A | 7/1994 | Fernandes et al. |
| 5,335,260 A | 8/1994 | Arnold |
| 5,341,101 A | 8/1994 | Maerefat et al. |
| 5,400,384 A | 3/1995 | Fernandes et al. |
| 5,600,700 A | 2/1997 | Krug et al. |
| 5,848,115 A | 12/1998 | Little et al. |
| 5,882,351 A | 3/1999 | Fox |
| 6,041,096 A | 3/2000 | Doi et al. |
| 6,061,425 A | 5/2000 | Sato |
| 6,231,231 B1 | 5/2001 | Farrokhnia et al. |
| 6,287,310 B1 | 9/2001 | Fox |
| 6,398,408 B1 | 6/2002 | Polkus |

(Continued)

*Primary Examiner*—Irakli Kiknadze
(74) *Attorney, Agent, or Firm*—McAndrews, Held & Malloy, Ltd.; Peter J. Vogel; Michael A. Dellapenna

(57) ABSTRACT

Certain embodiments of the present invention provide an improved system and method for detecting an alignment error in an imaging system. The method includes projecting a calibration pattern from a source onto a detector to generate calibration image data, and analyzing the calibration image data to determine a positional shift in the detector with respect to the source. The calibration pattern is generated by the imaging system using a calibration pattern generator, such as collimator or pattern insert, and the calibration pattern provides information regarding a position of the detector with respect to the source. An error may be reported if the calibration image data does not match the reference image data. An offset may be extracted based on a difference between the calibration image data and the reference image data to correct the positional shift. The offset may be automatically applied to imaging calculations from the imaging system.

20 Claims, 8 Drawing Sheets

U.S. PATENT DOCUMENTS

| | | |
|---|---|---|
| 6,457,861 B1 | 10/2002 | Petrick et al. |
| 6,459,765 B1 | 10/2002 | Ganin et al. |
| 6,470,207 B1 | 10/2002 | Simon et al. |
| 6,491,430 B1 | 12/2002 | Seissler |
| 6,501,819 B2 | 12/2002 | Unger |
| 6,533,455 B2 | 3/2003 | Graumann et al. |
| 6,585,412 B2 | 7/2003 | Mitschke |
| 6,600,805 B2 | 7/2003 | Hansen |
| 6,694,047 B1 | 2/2004 | Farrokhnia et al. |
| 6,739,751 B2 * | 5/2004 | Williams .................... 378/205 |
| 6,893,157 B2 * | 5/2005 | Arakawa .................... 378/205 |
| 7,197,830 B2 * | 4/2007 | Vaccaro ....................... 33/286 |

* cited by examiner

METHOD AND APPARATUS TO DETECT AND CORRECT ALIGNMENT ERRORS IN X-RAY SYSTEMS USED TO GENERATE 3D VOLUMETRIC IMAGES

BACKGROUND OF THE INVENTION

The present invention generally relates to definition of an image field of view. In particular, the present invention relates to a system and method for interactive definition of an image field of view in digital radiography.

Digital imaging systems may be used to capture images to assist a physician in making an accurate diagnosis. Digital radiography imaging systems typically include a source and a detector. Energy, such as x-rays, produced by the source travel through an object to be imaged and are detected by the detector. An associated control system obtains image data from the detector and prepares a corresponding diagnostic image on a display.

One or more collimators may be used to block and/or restrict x-rays or other energy directed at a detector. For example, collimator blades may be used to form an opening through which x-rays pass from a source to a detector. An example of sizing and aligning collimator blades may be found in U.S. Pat. No. 6,215,853, entitled "Apparatus and Method for X-ray Collimator Sizing and Alignment", which is herein incorporated by reference in its entirety.

The detector may be an amorphous silicon flat panel detector, for example. Amorphous silicon is a type of silicon that is not crystalline in structure. Image pixels are formed from amorphous silicon photodiodes connected to switches on the flat panel. A scintillator is placed in front of the flat panel detector. For example, the scintillator receives x-rays from an x-ray source and emits light of an intensity related to the amount of x-rays absorbed. The light activates the photodiodes in the amorphous silicon flat panel detector. Readout electronics obtain pixel data from the photodiodes through data lines (columns) and scan lines (rows). Images may be formed from the pixel data. Images may be displayed in real time. Flat panel detectors may offer more detailed images than image intensifiers. Flat panel detectors may allow faster image acquisition than image intensifiers depending upon image resolution.

A solid state flat panel detector typically includes an array of picture elements (pixels) composed of Field Effect Transistors (FETs) and photodiodes. The FETs serve as switches, and the photodiodes are light detectors and image storage elements. The array of FETs and photodiodes may be composed of amorphous silicon. A compound such as Cesium Iodide (CsI) is deposited over the amorphous silicon. CsI absorbs x-rays and converts the x-rays to light. The light is then detected and stored by the photodiodes. The photodiode acts as a capacitor and stores the charge.

Initialization of the detector occurs prior to an exposure. During an initialization of the detector, the detector is "scrubbed" prior to an exposure. During scrubbing, each photodiode is charged to a known bias voltage that represents "black", or no light output. The detector is then exposed to x-rays which are absorbed by the CsI deposited on the detector. Light that is emitted by the CsI in proportion to x-ray flux causes the affected photodiodes to conduct, partially discharging the photodiode. After the conclusion of the x-ray exposure, the voltage on each photodiode is gated through a FET switch to an analog voltage comparator, which compares the photodiode's stored voltage with the voltage generated from a digital to analog (D/A) converter. The digital input to the D/A converter begins at '0' and is incremented through a programmable ramp to a maximum value. As the analog ramp increases on the output of the D/A converter, the output eventually equals or exceeds the voltage coming from the photodiode, at which time the analog voltage comparator latches the current value of the D/A converter, which represents the digital pixel value for that photodiode.

The detector is read or scrubbed according to the array structure. That is, the detector is read on a scan line by scan line basis. A FET switch associated with each photodiode is used to control reading of photodiodes on a given scan line. Reading is performed whenever an image produced by the detector includes data, such as exposure data and/or offset data. Scrubbing occurs when data is to be discarded from the detector rather than stored or used to generate an image. Scrubbing is performed to maintain proper bias on the photodiodes during idle periods. Scrubbing may also be used to reduce effects such as incomplete charge restoration of the photodiodes, for example. Scrubbing restores charge to the photodiodes but the charge may not be measured. If the data is measured during scrubbing, the data may simply be discarded.

Switching elements in a solid state detector minimize a number of electrical contacts made to the detector. If no switching elements are present, at least one contact for each pixel is present on the detector. Lack of switching elements may make the production of complex detectors prohibitive. Switching elements reduce the number of contacts to no more than the number of pixels along the perimeter of the detector array. The pixels in the interior of the array are "ganged" together along each axis of the detector array. An entire row of the array is controlled simultaneously when the scan line attached to the gates of the FETs of pixels on that row is activated. Each of the pixels in the row is connected to a separate data line through a switch. The switch is used by read out electronics to restore charge to the photodiode. As each row is activated, all of the pixels in the row have the charge restored to the respective photodiodes simultaneously by the read out electronics over the individual data lines. Each data line typically has a dedicated read out channel associated with the data line.

Additionally, the detector electronics may be constructed in basic building blocks to provide modularity and ease of reconfiguration. Scan drivers, for example, may be modularized into a small assembly that incorporates drivers for 256 scan lines, for example. The read out channels may be modularized into a small assembly that would read and convert the signals from, for example, 256 data lines. The size, shape, architecture and pixel size of various solid state detectors applied to various imaging systems determine the arrangement and number of scan modules and data modules to be used.

A control board is used to read the detector. Programmable firmware may be used to adapt programmable control features of the control board for a particular detector. Additionally, a reference and regulation board (RRB) may be used with a detector to generate noise-sensitive supply and reference voltages (including a dynamic conversion reference) used by the scan and data modules to read data. The RRB also distributes control signals generated by the control board to the modules and collects data returned by the data modules. Typically, the RRB is designed specifically for a particular detector. An interface between the control board and the RRB may be implemented as a standard interface such that signals to different detectors are in a similar format.

Three-dimensional (3D) volumetric imaging (example shown in FIG. 1) provides new diagnostic and clinical analysis tools to physicians. 3D images are created by acquiring a series of two-dimensional (2D) images at predetermined positions along an arc about a patient. Software applications using complex mathematical processes extract volume elements or "voxels" from the 2D images by using the image content (e.g., a black-and-white x-ray image) and positional information (e.g., where the image was positioned along an arc). The voxels may then be assembled into a three-dimensional image and then viewed from any angle.

Due to the complex mathematics involved, it is important that the x-ray source be as directly centered above the x-ray detector and that the detector be as precisely perpendicular in both the X and Y planes of the beam as possible. The positional tolerances for mechanical mounting are typically small, in the range of ±0.5 mm (about twelve-thousandths of an inch).

Additionally, many imaging products are mobile, which offers hospitals, clinics, and physicians the ability to move these systems from room-to-room or to bring x-ray capability to a patient that cannot be moved. With the benefit of mobility also comes the risk of collision. Even if the systems are stationary, an accidental collision with a patient or operator may shift the detector. Due to the extremely tight tolerances required for 3D volumetric imaging, even small collisions may cause shifts in the x-ray detector and result in the degradation or deformation of the resulting 3D image. Traditional camera-based detector systems do not provide positional locating ability and may operate with a drift of several picture elements or "pixels" in position. Because these shifts may be imperceptible to the human eye, it would be highly desirable to know if the x-ray detector has shifted, and very advantageous to be able to automatically correct for any positional errors that may occur.

Furthermore, the Food and Drug Administration (FDA) places limits on radiation exposure to patients. The FDA is concerned with radiating a patient and being unable to use the resulting image due to calibration errors in the imaging system. Thus, a system and method which reduce a number of unusable images would be highly desirable.

Therefore, there is a need for an improved method and system for detecting alignment errors in imaging systems. Further, there is a need for an improved method and system for correcting alignment errors in imaging systems.

BRIEF SUMMARY OF THE INVENTION

Certain embodiments of the present invention provide an improved system and method for detecting an alignment error in an imaging system. Certain embodiments provide a method including projecting a calibration pattern from a source onto a detector along an axis between the source and the detector to generate calibration image data, and comparing the calibration image data to reference image data to determine a positional shift in the detector with respect to the source. In certain embodiments, the calibration image data may be analyzed to determine positional shift without comparison to reference image data. The calibration pattern is generated by the imaging system using a calibration pattern generator, such as a collimator or pattern insert, and the calibration pattern provides information regarding a position of the detector with respect to the source.

In an embodiment, an error is reported if the calibration image data does not match the reference image data. An offset may be extracted based on a difference between the calibration image data and the reference image data to correct the positional shift. An offset may also be calculated by analyzing a calibration image. In an embodiment, the offset is automatically applied to imaging calculations from the imaging system. In an embodiment, the positional shift of the detector with respect to the source is automatically determined. In an embodiment, the positional shift includes a horizontal positional shift, a vertical positional shift, and/or a rotational positional shift, for example.

The imaging system may be an x-ray imaging system, for example, and the axis may be an axis along which x-rays are projected from the source to the detector to generate image data. In an embodiment, the imaging system may provide three dimensional volumetric imaging, for example.

Certain embodiments provide a system for calibrating a detector position with respect to a source. The system includes a digital detector capable of generating image data in response to a beam impinging upon the detector, a source configured to project the beam onto the detector, a calibration pattern generator configured to project a calibration pattern onto the detector, and a data processing unit for obtaining image data from the calibration image and analyzing the image data, such as by comparing the image data from the calibration image to reference image data. The calibration pattern is used to determine a positional shift of the detector with respect to the source. In an embodiment, the calibration pattern generator may include a collimator and/or a pattern insert, for example.

In an embodiment, the calibration pattern includes a crosshair calibration pattern, an oval calibration pattern, a circular calibration pattern, a square calibration pattern, and/or a rectangular calibration pattern, for example. The collimator may be configured with the calibration pattern manually and/or automatically. In an embodiment, the positional shift includes a horizontal positional shift, a vertical positional shift, and/or a rotational positional shift, for example.

In an embodiment, the system is configured to automatically project the calibration pattern onto the digital detector and compare the image data from the calibration image to reference image data to determine a positional shift of the detector with respect to the source. In an embodiment, the data processing unit determines the positional shift of the detector by comparing the image data from the calibration image to reference image data and generates correctional data for use in image processing. The data processing unit alerts an operator and/or a system that the detector has shifted with respect to the source.

Certain embodiments provide a computer-readable storage medium including a set of instructions for a computer. The set of instructions includes a data acquisition routine configured to acquire calibration image data from a digital detector corresponding to a calibration image projected onto the detector; and a calibration routine analyzing the calibration image data (e.g. comparing the calibration image data to reference image data indicating a desired positioning on the detector). The calibration routine identifies a positional shift of the detector with respect to an imaging source based on the comparison. The set of instructions may also include a projection routine configured to manipulate a collimator or pattern insert to project a calibration pattern from the imaging source onto the detector to form the calibration image. The set of instructions may also include a correction routine configured to adjust processing of image data from the detector based on the positional shift. In an embodiment, the calibration routine generates an alert indicating the positional shift of the detector.

Figure 1:
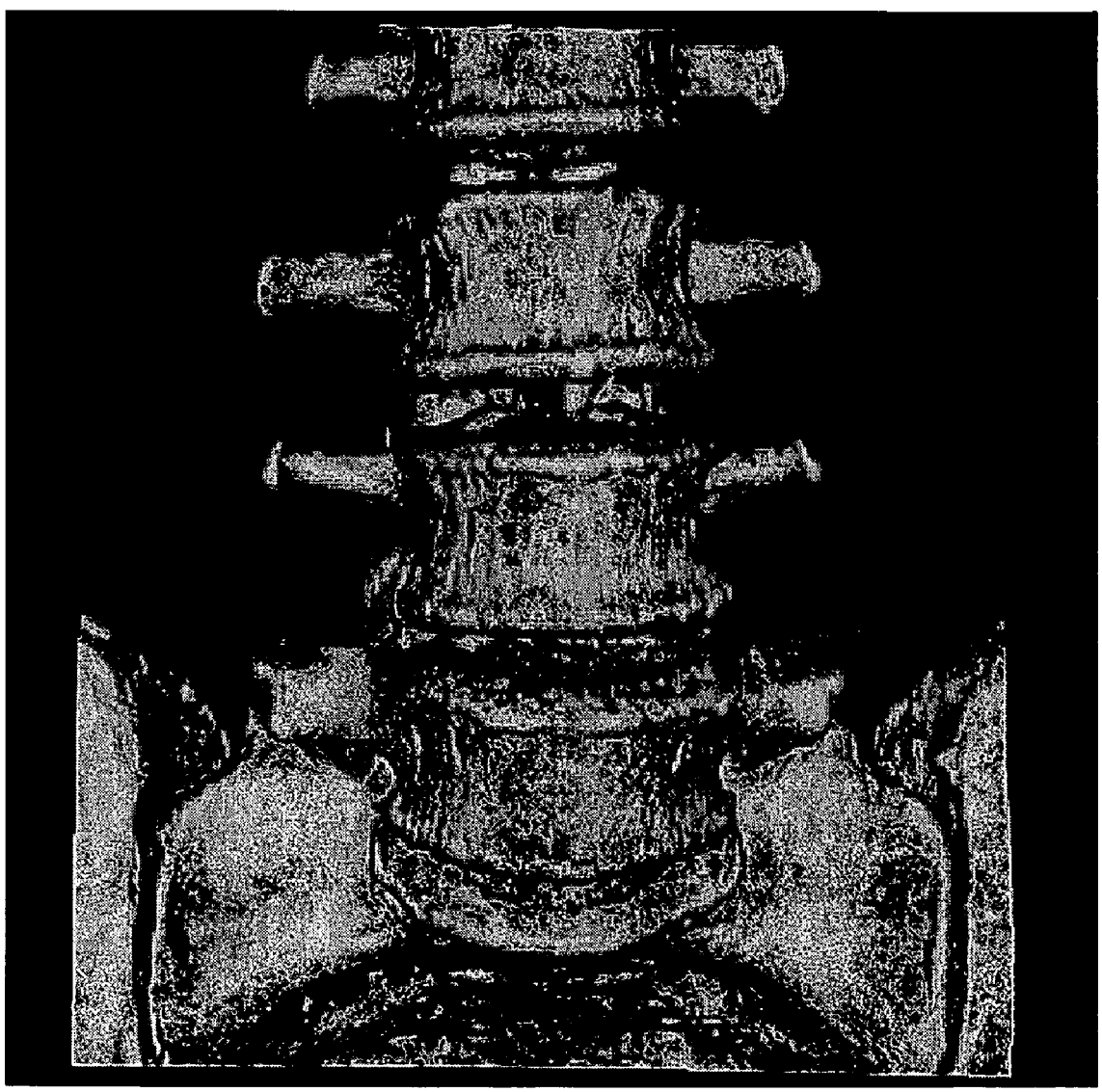
FIG. 1 depicts an example of a three-dimensional (3D) volumetric imaging.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Figure 2:
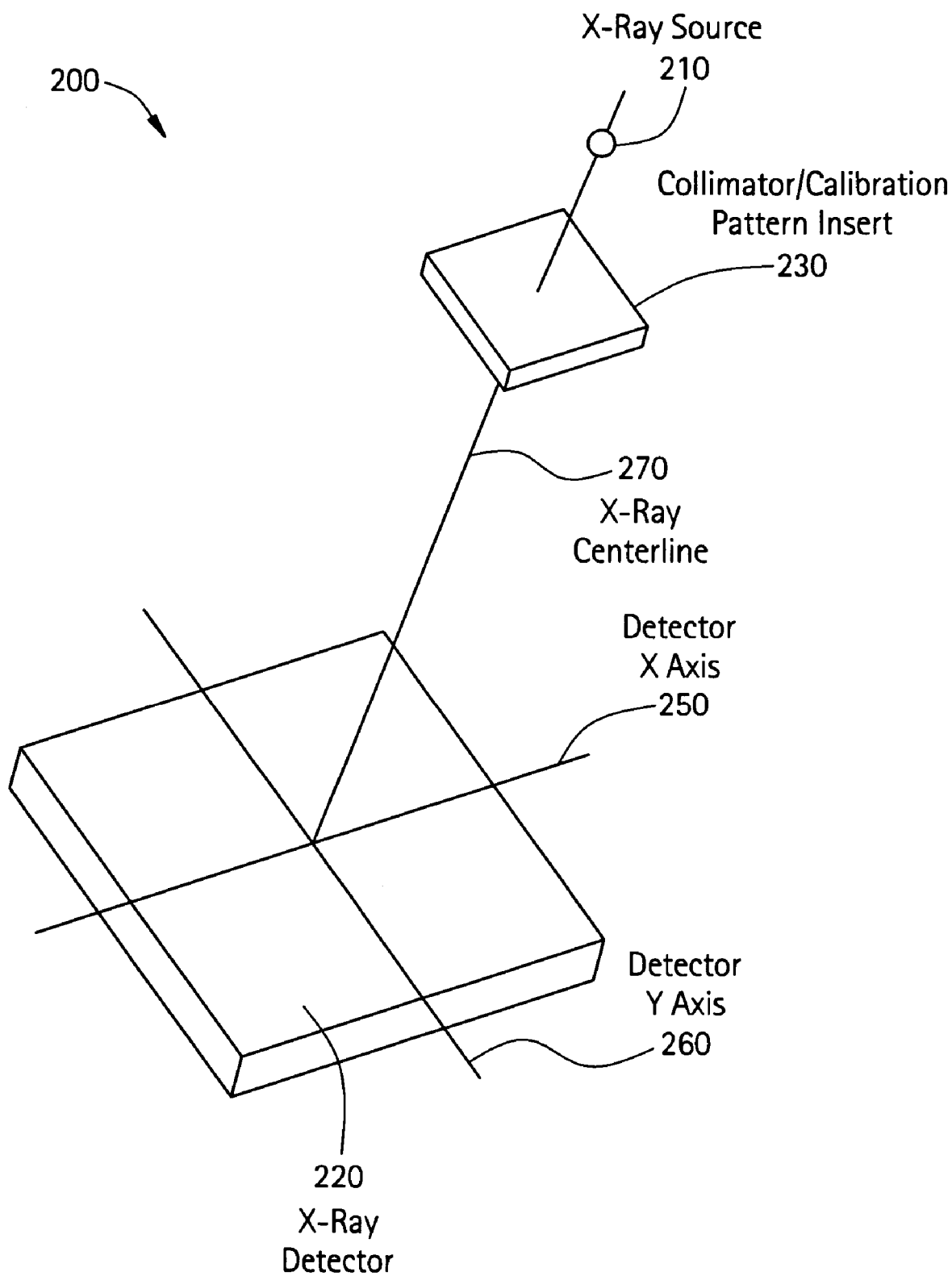
FIG. 2 illustrates an imaging system used in accordance with an embodiment of the present invention.

FIG. 2 illustrates an imaging system 200 used in accordance with an embodiment of the present invention. The imaging system 200 includes a plurality of subsystems. For the purposes of illustration, the imaging system 200 is described as an x-ray system. The imaging system 200 includes subsystems, such as an x-ray source 210, an x-ray detector 220, and a calibration pattern generator 230 (e.g., a collimator or pattern insert). The imaging system 200 may also include a data acquisition system 240 with read out electronics 245 (not shown). In an embodiment, a scintillator, such as a screen, is positioned in front of the detector 220. In an embodiment, the detector 220 is an amorphous silicon flat panel detector. An object such as a patient or other object to be imaged may be positioned in front of the detector 220.

The object is positioned in imaging system 200 for imaging. In one exemplary system, an x-ray source 210 is positioned above the object. The x-ray detector 220 is positioned below the object. A scintillator may be positioned between the object and the x-ray detector 220. X-rays are transmitted from the x-ray source 210 through the collimator/pattern insert 230, then through the object to the scintillator. The scintillator emits light in response to the x-rays transmitted from the x-ray source 210 through the object. The emitted light is transmitted to the x-ray detector 220. For example, light emitted by the scintillator activates or discharges photodiodes in the detector 220. The read out electronics 245 may include a reference and regulation board (RRB) or other data collection unit. The RRB may accommodate and connect data modules to transfer data from the detector 220 to the data acquisition system 240. The read out electronics 245 transmit the data from the detector 220 to the data acquisition system 240. The data acquisition system 240 forms an image from the data and may store, display, and/or transmit the image. Pre-processing and processing functions may be applied to the acquired image before and/or after storage, display, and/or transmission, for example.

Certain embodiments provide a method and apparatus to recover x-ray beam and x-ray detector alignment/calibration information from the x-ray system 200 in the form of a digital image. Mathematical algorithms applied to the image are used to determine whether or not the x-ray system 200 is aligned and calibrated within tolerances for 3D volumetric image reconstruction. In an embodiment, alignment and calibration of the x-ray system 200 may be automated.

In an embodiment, a precision square collimator 230 is used to automatically project a crosshair calibration pattern onto the x-ray detector 220. A square collimator 230 may generate basic calibration patterns with straight edges, for example. Alternatively, a calibration pattern may be implemented in a lead panel or insert and inserted between the x-ray source 210 and the x-ray detector 220. Calibration patterns implemented using an insert or other marker may be complex patterns, with circular and/or straight edges that may help determine rotational axis errors, for example.

Calibration verification processes may be automatically executed as part of a 3D sweep or other operation to confirm orientations between the x-ray source 210 and the x-ray detector 220. Out-of-calibration conditions are detected and appropriate user interactions performed (warnings, error states, logging, correction, etc.). Calibration tolerances may be applied, such that if the calibration is outside of specified tolerances, action may be taken. In an embodiment, some out-of-calibration conditions may be detected and corrected by extracting offset or delta values and proving correction data to the 3D volumetric rendering or other image correction processes.

The system 200 illustrated in FIG. 2 may be used to detect and correct alignment errors. As described above, the x-ray source 210 emits x-rays through the calibration pattern generator (e.g., collimator/calibration pattern insert) 230 and down to the x-ray detector 220. The x-ray detector apparatus 220 is used to detect and create an image from the x-ray source 210. The detector's imaging plane is an array of detector elements organized in a grid. The elements are organized in rows and columns, and the detector 220 has both an X axis 250 and a Y axis 260. The x-ray centerline 270 is represented as a vector that runs from the x-ray source 210 through the collimator/calibration pattern insert 230 and down to the x-ray detector 220. For 3D imaging, the centerline 270 should be as close as possible to perpendicular to both the X axis 250 and Y axis 260 of the detector 220 for 3D imaging.

The calibration pattern generator 230 is set to a desired area of illumination on the x-ray detector 220. When the x-ray source 210 is energized, x-rays are emitted and directed down through the calibration pattern generator 230 towards the x-ray detector 220. Only x-rays that can pass through the open area of the calibration pattern generator 230 may illuminate the x-ray detector 220. Other x-rays are blocked by the calibration pattern generator 230.

The following is one example of detecting and correcting an out-of-calibration state in the system 200 for 2D and/or 3D image acquisition. Before a 2D image is taken, or a 3D sweep is performed, the system 200 confirms proper calibration between the x-ray source 210 and x-ray detector 220. Calibration may be performed manually, and/or by a processor in communication with the detector 220 or other portion of the system 200. The detector 220 is scrubbed (e.g., image information is erased digitally) by the data acquisition system 240 (e.g., by the read out electronics 245) in preparation for imaging.

Figure 3:
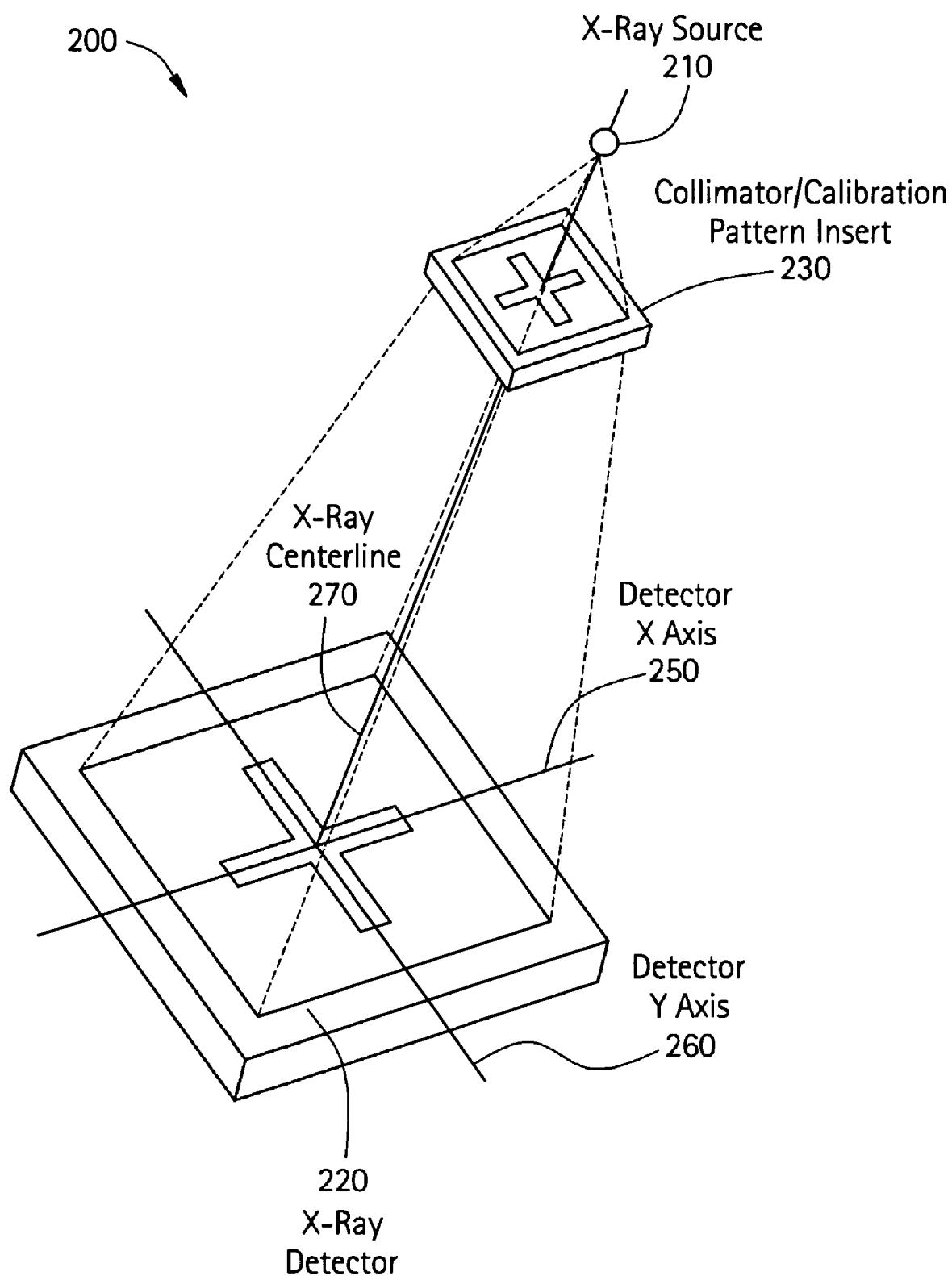
FIG. 3 shows an example of projecting a calibration pattern onto an x-ray detector in accordance with an embodiment of the present invention.

The calibration pattern generator (e.g., collimator, pattern insert or other marker) 230 is set to project a narrow vertical rectangle of predetermined size onto the detector 220, and the x-ray source 210 is turned on for a pre-determined amount of time. X-rays from the source 210 write a vertical portion of a crosshair to the detector 220. Then, the pattern generator 230 is set to project a narrow horizontal rectangle of predetermined size onto the detector 220, and the x-ray source 210 is turned on for a pre-determined amount of time to produce a horizontal portion of the crosshair to the detector 220 and completes the calibration pattern generation process. An example of projecting a calibration pattern onto the x-ray detector 220 is shown in FIG. 3.

An image is extracted from the detector using the read out electronics 245, and simple image processing techniques are applied to determine the extent of the crosshair. The image may be processed to remove noise, for example, and to adjust the image so that only pixels above a certain threshold are considered "illuminated". Other pixels may be considered "dark". The extent and shape of the crosshair may be extracted after processing.

Then, the position of the crosshair in the image is compared to the horizontal and vertical centerlines on the X and Y axes 250, 260. The crosshair should overlay the center of the detector 220 at the x-ray centerline 270 (within a specified tolerance) or a calibration error may be flagged. The height of the vertical portion of the crosshair is calculated. The width of the horizontal portion of the crosshair is calculated. The two values are then compared. The height of the vertical portion and the width of the horizontal portion should be equal to each other (within a specified tolerance) or a calibration error may be flagged.

If a shift in vertical or horizontal position has occurred but the panel appears to be perpendicular to the x-ray source 210 (the crosshair is not centered on the detector 220 within tolerance but the height of the vertical portion is equal to the width of the horizontal portion within tolerance), then a correction may be performed. Other errors may similarly result in a correction. A difference (delta) between the true image center and the projected center is calculated and the offset value(s) are made available to the 3D volumetric rendering processes or other image correction processes, for example. After calibrating, a 3D sweep process may begin.

A variety of methods may be used to project a calibration test pattern onto the x-ray detector 220. For example, a lead panel or other insert may be used as a calibration pattern insert. The lead panel includes a cutout or opening in the shape of the pattern to be projected onto the detector 220. In FIG. 3, a crosshair calibration pattern is shown, but other patterns, such as a circle, oval, square, or rectangle, may be used. As another example, a precision collimator may be used to create the crosshair pattern automatically. The horizontal and vertical shutters in the square collimator may be positioned to create the vertical component of the crosshair. After an x-ray exposure, the collimator shutters may be positioned to create the horizontal component of the crosshair.

Certain embodiments include a variety of methods of projecting a calibration marker onto the x-ray detector 220 along the same axis as the x-rays are emitted. For example, a laser marker may be used to project a visible marker onto the detector 220, or the x-ray source 210 may utilize a lead shutter to project a marker onto the detector 220 using x-rays. Alternatively, a lead panel with a patterned opening (such as an oval, a circle, a rectangle, a square, a curved, a straight and/or other geometrically-shaped opening) may be positioned between the source 210 and detector 220. The pattern in the panel is projected onto the detector 220. In another embodiment, one or more collimators with moveable doors are positioned between the source 210 and the detector 220. A system and/or software program may be used to position the doors to project a cross (a horizontal line and a vertical line) or other shape, for example. In an embodiment, the collimator doors may be automatically positioned for calibration.

After the x-ray detector 220 has been exposed with a test pattern, data relating to the test pattern may be extracted from the x-ray detector 220 and analyzed. The shape and size of the calibration pattern determines the accuracy to which errors in alignment may be detected, and the accuracy with which the alignment errors may be corrected.

In an embodiment, the data acquisition system 240, or data processing unit, may include instructions to facilitate calibration of the imaging system 200. For example, the set of instructions may include a data acquisition routine configured to acquire calibration image data from a digital detector corresponding to a calibration image projected onto the detector; and a calibration routine comparing the calibration image data to reference image data indicating a desired positioning on the detector. The calibration routine identifies a positional shift of the detector with respect to an imaging source based on the comparison. The set of instructions may also include a projection routine configured to manipulate a collimator to project a calibration pattern from the imaging source onto the detector to form the calibration image. The set of instructions may also include a correction routine configured to adjust processing of image data from the detector based on the positional shift. In an embodiment, the calibration routine generates an alert indicating the positional shift of the detector.

Figure 4:
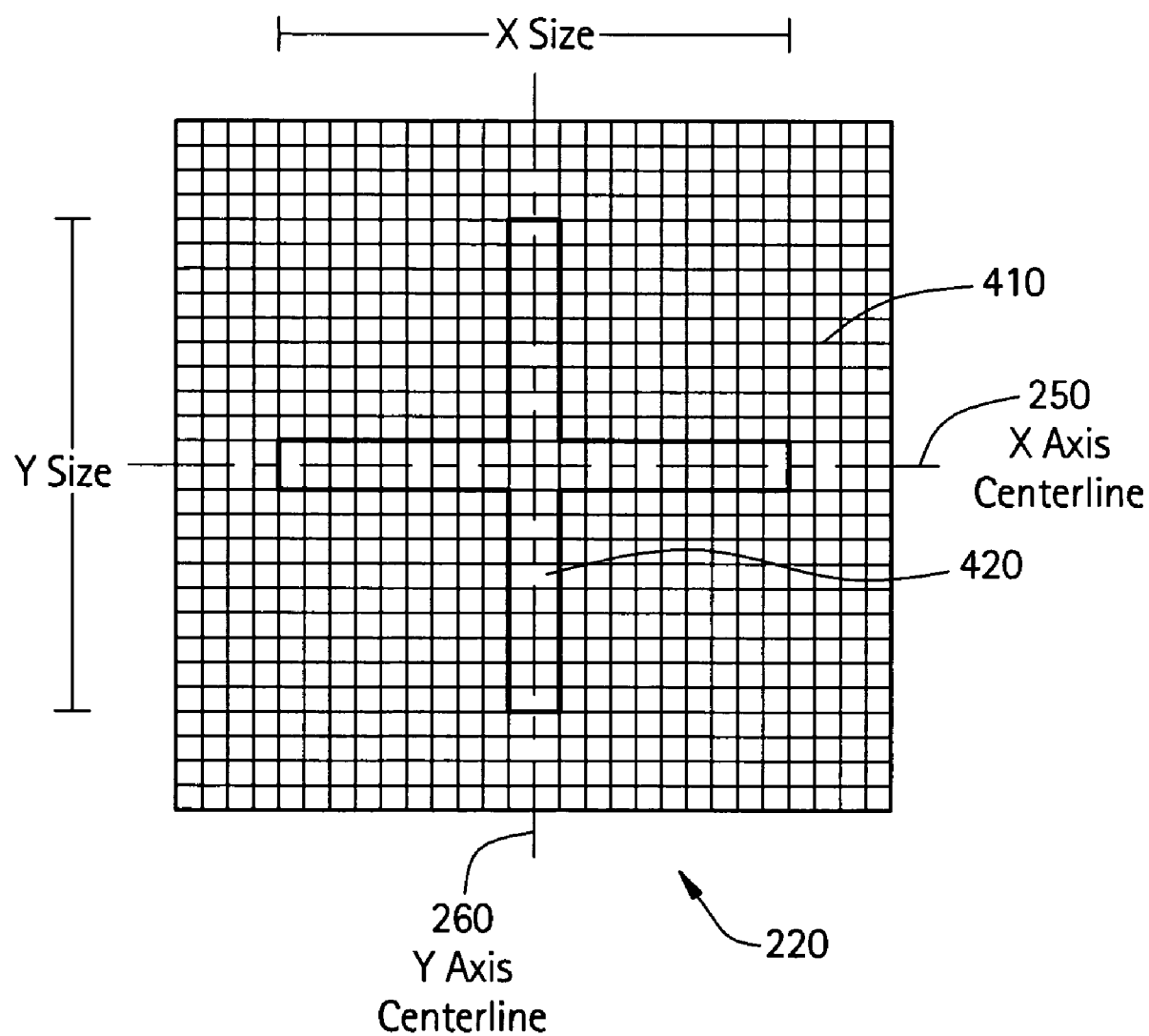
FIG. 4 illustrates an example of a properly aligned x-ray system according to an embodiment of the present invention.

FIG. 4 illustrates an example of a properly aligned x-ray system 200. The grid 410 shown on the detector 220 in FIG. 4 represents individual x-ray imaging elements in the detector 220 used to detect x-rays and create an image. In this example, the calibration pattern is a simple crosshair 420. The crosshair 420 is properly aligned on the center of both the X and Y axis 250, 260, indicating that the x-ray detector 220 is centered in the x-ray beam. The width and height of the crosshair 420 are equal, indicating that there is no tilt in either axis, and that the x-ray centerline 270 is perpendicular to the imaging plane of the x-ray detector 220.

Figure 5:
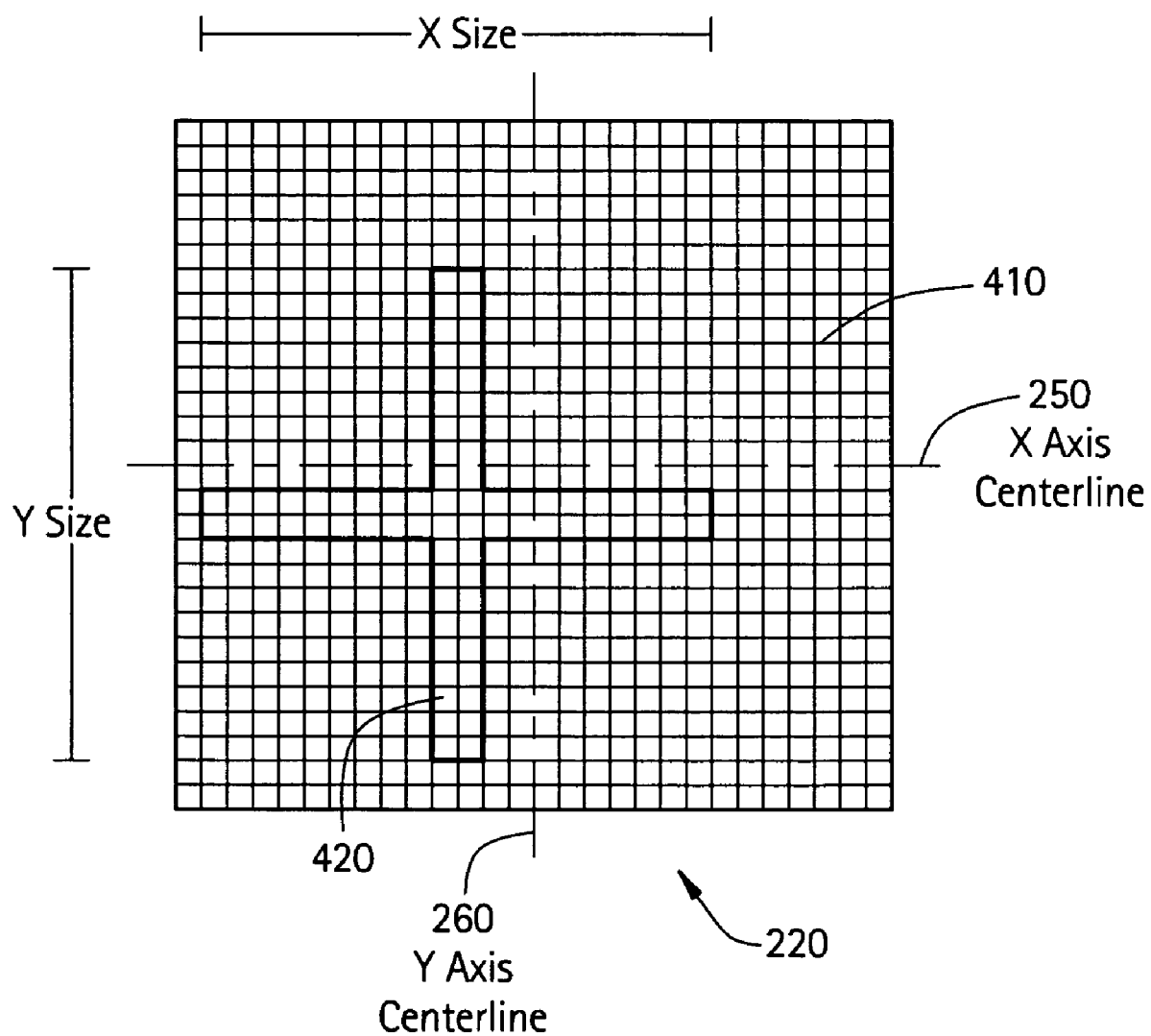
FIG. 5 illustrates an example of an improperly aligned x-ray system according to an embodiment of the present invention.

FIG. 5 illustrates an example of an improperly aligned x-ray system. Using the same calibration pattern (the crosshair) from the previous example, a shift of the x-ray detector 220 and/or the x-ray source 210 with respect to each other may be seen. The x-ray detector 220 shows that an offset has occurred of −3 pixels in the X axis 250 and −2 pixels in the Y axis 260. The width and height of the crosshair 420 are equal, meaning that a simple shift has occurred and that the x-ray centerline 270 is still perpendicular to the imaging plane of the x-ray detector 220. The calibration image of the crosshair 420 shows that a shift has occurred, and a variety of warnings, error reports, log entries, and/or other mechanisms may be used to alert an operator or system of the shift. Because the x-ray centerline 270 is perpendicular to the x-ray detector imaging plane (i.e. no tilt or rotation about either the X or Y axis has occurred), correctional values may be extracted from the calibration image and used by the processes used to create the 3D volumetric imagery to compensate for the shift in detector 220 and/or source 210 position. For example, a number of pixels difference between the calibration image and the expected image may be determined and used to adjust acquired image data. In an embodiment, if an oval or circle, for example, is used instead of a crosshair, a width and height of the pattern may be measured to determine a calibration offset.

Figure 6:
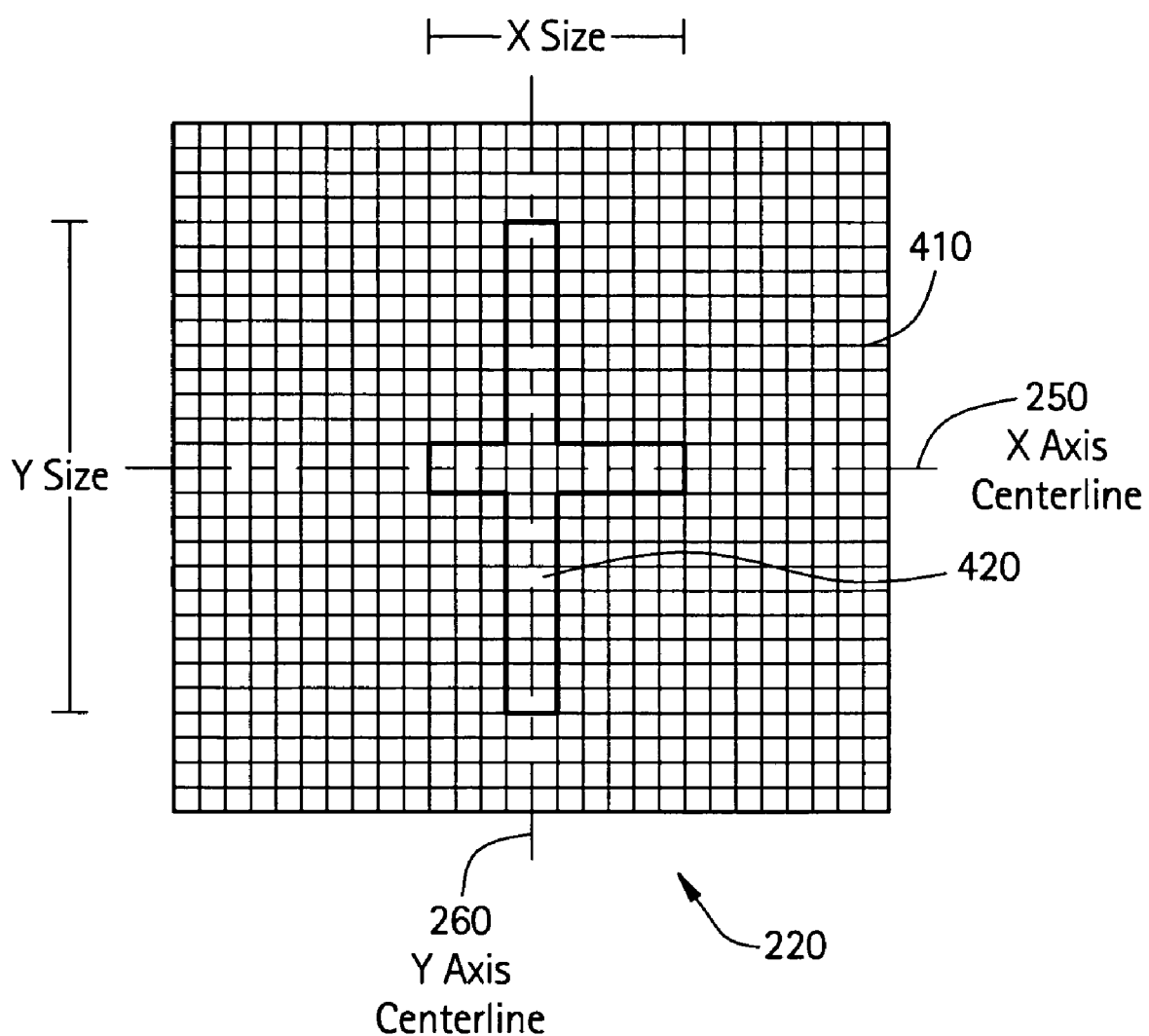
FIG. 6 shows another example of an improperly aligned x-ray system according to an embodiment of the present invention.

FIG. 6 shows another example of an improperly aligned x-ray system. Using the same calibration pattern (the crosshair) from the previous examples, rotation of the x-ray detector 220 or the x-ray source 210 about the Y axis 260 may be detected. In this example, the distorted crosshair appears to be aligned properly to the center of the detector 220, which indicates that no shifting has occurred. But because the width and height of the crosshair 420 do not match, the x-ray detector 220 has rotated and the imaging plane of the detector is no longer perpendicular to the x-ray beam. In an embodiment, a variety of warnings, error reports, log entries, and/or other mechanisms may be used to alert an operator and/or system of the error.

In an embodiment, a crosshair pattern may not provide enough information as to which axis is off or the direction(s) of rotation. The error condition(s) may be flagged and/or reported to an operator, log and/or system. Other types of calibration patterns, such as a circle, oval, square or rectangle, may be created to contain enough orientation information to extract correction data to compensate for one or more calibration errors during 2D and/or 3D imaging. For example, a shape of an oval calibration pattern may be measured to determine a twist of the detector 220 with respect to the x-ray source 210 (or vice versa). An offset may be identified and applied to correct image data.

Figure 7:
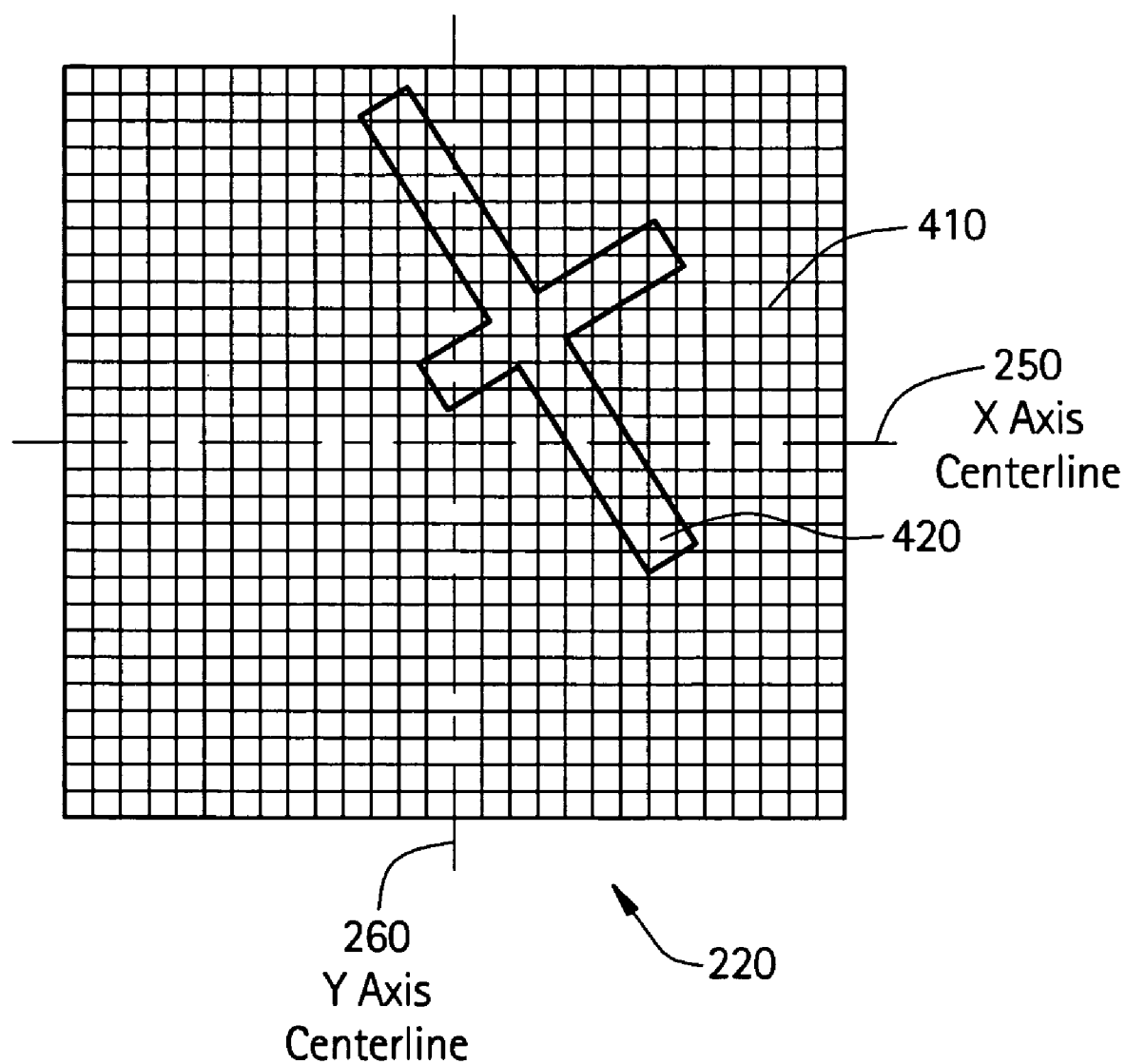
FIG. 7 depicts another example of an improperly aligned x-ray system according to an embodiment of the present invention.

FIG. 7 depicts another example of an improperly aligned x-ray system according to an embodiment of the present invention. Using the same calibration pattern (the crosshair) from the previous examples, multiple calibration errors may be detected with respect to the x-ray detector 220 and/or the x-ray source 210. In response to the calibration error(s) (off center, plane rotation, etc.), a variety of warnings, error reports, log entries, and/or other mechanisms may be used to alert an operator and/or system of the error condition.

In an embodiment, a crosshair pattern may not provide enough information as to which axis is off or the direction(s) of rotation. The error condition(s) may be flagged and/or reported to an operator, log and/or system. Other types of calibration patterns, such as a circle, oval, square or rectangle, may be created to contain enough orientation information to extract correction data to compensate for one or more calibration errors during 2D and/or 3D imaging. For example, multiple ovals may be used to determine a twisting or offset in the system 200 and apply the offset to image data.

Figure 8:
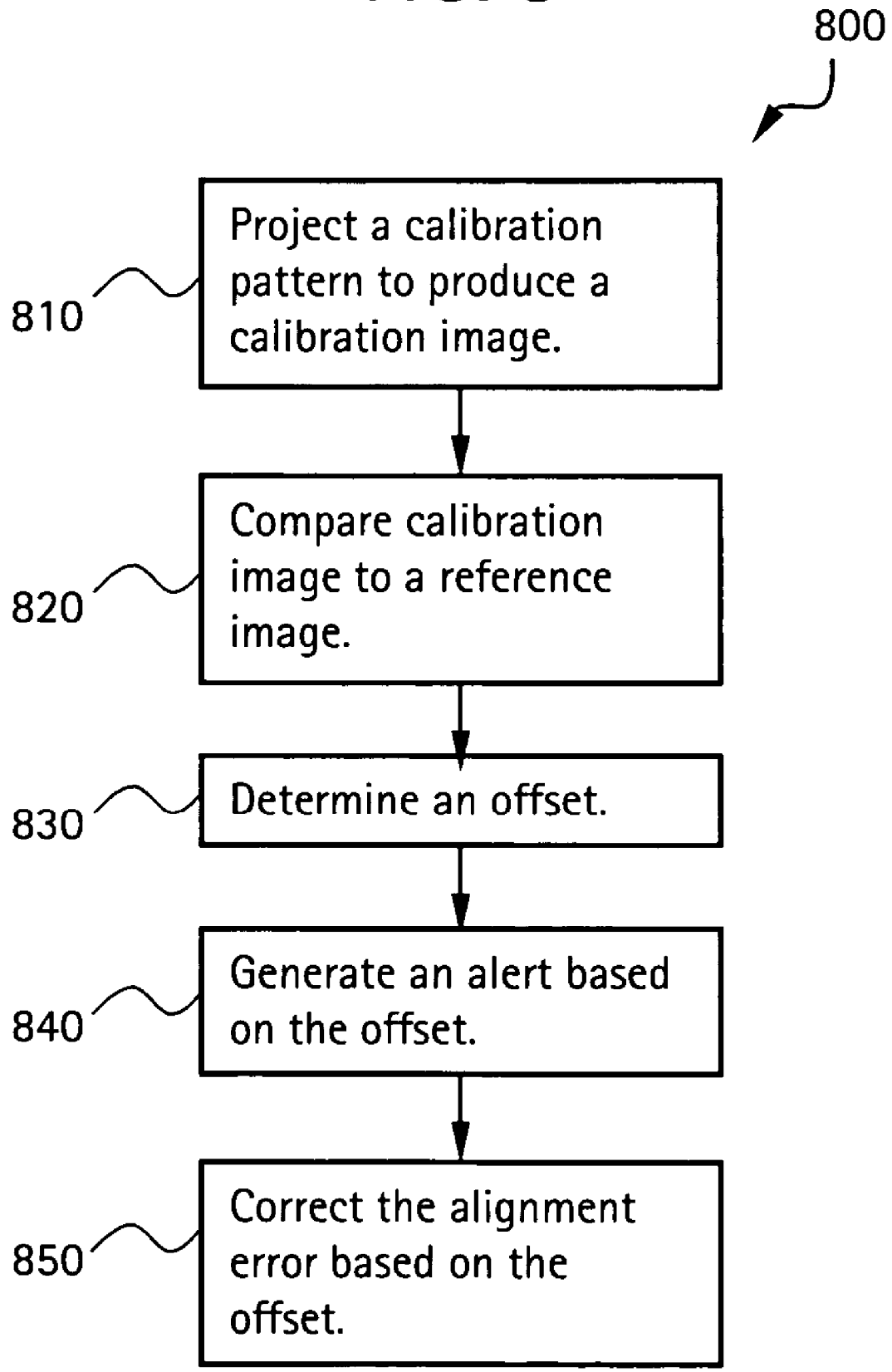
FIG. 8 illustrates a flow diagram for a method for identifying and correcting alignment errors in an imaging system in accordance with an embodiment of the present invention.

FIG. 8 illustrates a flow diagram for a method 800 for identifying and correcting alignment errors in an imaging system in accordance with an embodiment of the present invention. First, at step 810, a calibration pattern is projected onto the detector 220 to produce a calibration image. For example, a crosshair is manually or automatically projected onto the detector 220 using the source 210 and the calibration pattern generator 230. Then, at step 820, the calibration image is analyzed, or may be compared to a reference image. For example, an image of the calibration crosshair is compared to a reference crosshair image centered on the detector 220.

Next, at step 830, a variance or offset is determined. For example, pixel locations may be compared to determine a difference between the calibration image and the reference image. Alternatively, an offset may be determined by analyzing the calibration without comparison to a reference image. At step 840, an alert may be generated based on the offset. For example, a visual, audio, and/or recorded alert may be generated. An alert may be relayed to an operator, a system, a log, etc. The alert may indicate the presence of an alignment error and/or may provide details of the error, for example. Then, at step 850, the alignment error may be corrected based on the offset. For example, the alignment error may be corrected and/or compensated for by adjusting acquired image data using the offset and/or correcting the misalignment in the imaging system. The error may be corrected manually and/or automatically.

In an embodiment, one or more of steps 840 and 850, alert and/or correction of the alignment error, may be optional. That is, an error may be identified and an alert sent, but a correction not performed. Alternatively, an error may be identified and corrected without an alert being generated.

Thus, certain embodiments of the present invention provide physicians, radiologists, and other medical personnel with a system and method to help validate and confirm that an x-ray system or similar imaging system is properly calibrated and that 2D image quality and/or 3D volumetric image quality is within specifications for clinical and diagnostic applications. Certain embodiments provide an imaging system that may automatically detect calibration problems that are imperceptible to the human eye but that may still result in poor image quality and degradation. Certain embodiments provide a system that may automatically detect calibration problems and report an "out-of-calibration" status to an operator. Certain embodiments provide a system that may automatically correct some calibration problems and allows normal machine operations in situations that might otherwise cause "downtime" while field-service personnel are called in to re-align and correct problems. Additionally, a system and method for automatically correcting at least some calibration errors offers greater system reliability, longer time between scheduled service calls, and cost savings.

Certain embodiments use of a collimator to create a crosshair calibration pattern on an x-ray detector. Other embodiments use square and/or round collimators to constrain an x-ray beam to create a machine recognizable pattern. Certain embodiments use an x-ray generated calibration image to determine whether or not the image is perpendicular to the x-ray beam. Certain embodiments use an x-ray generated calibration image to detect horizontal and vertical shifts of the x-ray detector relative to the x-ray beam. Additionally, certain embodiments use an x-ray generated calibration image to detect rotational shifts about the X and/or Y axis of the x-ray detector relative to the x-ray beam. Extraction of offset (delta) values may be used to correct horizontal and vertical shifts between the x-ray detector and the x-ray beam. Shifts may cause image reconstruction problems and poor image quality in 3D volumetric rendering. A calibration pattern may be embedded into a lead panel that is inserted between the x-ray image and the x-ray detector. Very complex calibration patterns may be created using this technique. Certain embodiments use equipment calibration patterns self-generated by the x-ray system to identify and/or correct system orientation problems.

Certain embodiments use automatic methods to calculate a detector positional shift and feed correctional data back into 3D volumetric and/or 2D calculations. An operator may be alerted that an x-ray detector has shifted and that 3D and/or 2D image quality may suffer. Calibration error detection and/or correction may be applied to stationary, mobile and/or C-arm imaging systems, for example.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method for detecting an alignment error in an imaging system, said method comprising:
projecting a calibration pattern from a source onto a detector along an axis between said source and said detector to generate calibration image data, wherein said calibration pattern is generated by the imaging system using a calibration pattern generator and wherein said calibration pattern provides information regarding a position of said detector with respect to said source;
analyzing said calibration image data to determine a positional shift in said detector with respect to said source;
wherein said calibration pattern generator further comprises a pattern insert.

2. The method of claim 1, further comprising reporting an error if said calibration image data does not match said reference image data.

3. The method of claim 1, further comprising extracting an offset based on said calibration image data to correct said positional shift.

4. The method of claim 3, wherein said offset is automatically applied to imaging calculations from the imaging system.

5. The method of claim 1, wherein said positional shift of said detector with respect to said source is automatically determined.

6. The method of claim 1, wherein said imaging system provides three dimensional volumetric imaging.

7. The method of claim 1, wherein said positional shift comprises at least one of a horizontal positional shift, a vertical positional shift, and a rotational positional shift.

8. The method of claim 1, wherein said step of analyzing further comprises comparing said calibration image data to reference image data to determine said positional shift.

9. The method of claim 1, wherein said calibration pattern comprises at least one of a crosshair calibration pattern, an oval calibration pattern, a square calibration pattern, and a rectangular calibration pattern.

10. The method of claim 1, further comprising alerting at least one of an operator and a system that said detector has shifted with respect to said source.

11. A system for calibrating a detector position with respect to a source, said system comprising:
a digital detector capable of generating image data in response to a beam impinging upon said detector;
a source configured to project the beam onto said detector;
a calibration pattern generator configured to project a calibration pattern onto said detector, wherein said calibration pattern is used to determine a positional shift of said detector with respect to said source; and
a data processing unit for obtaining image data from said calibration images, and analyzing said calibration image data to determine said positional shift;
wherein said calibration pattern generator further comprises pattern insert.

12. The system of claim 11, wherein said calibration pattern comprises at least one of a crosshair calibration pattern, an oval calibration pattern, a circular calibration pattern, a square calibration pattern, and a rectangular calibration pattern.

13. The system of claim 11, wherein said calibration pattern generator is automatically configured with said calibration pattern.

14. The system of claim 11, wherein said system is configured to automatically project said calibration pattern onto said digital detector and compare said image data from said calibration image to reference image data to determine a positional shift of said detector with respect to said source.

15. The system of claim 11, wherein said data processing unit determines said positional shift of said detector by comparing said image data from said calibration image to reference image data and generates correctional data for use in image processing.

16. The system of claim 11, wherein said data processing unit alerts at least one of an operator and a system that said detector has shifted with respect to said source.

17. The system of claim 11, wherein said positional shift comprises at least one of a horizontal positional shift, a vertical positional shift, and a rotational positional shift.

18. A computer-readable storage medium including a set of instructions for a computer, the set of instructions comprising:
a data acquisition routine configured to acquire calibration image data from a digital detector corresponding to a calibration image projected onto said detector; and
a calibration routine comparing said calibration image data to reference image data indicating a desired positioning on said detector, wherein said calibration routine identifies a positional shift of said detector with respect to an imaging source based on said comparison; and
a projection routine configured to manipulate a calibration pattern generator, said calibration pattern generator comprising a pattern insert, to project a calibration pattern from said imaging source onto said detector to form said calibration image.

19. The set of instructions of claim 18, further comprising a correction routine configured to adjust processing of image data from said detector based on said positional shift.

20. The set of instructions of claim 18, wherein said calibration routine generates an alert indicating said positional shift of said detector.

* * * * *